United States Patent [19]

Curtis et al.

[11] Patent Number: 5,824,780
[45] Date of Patent: Oct. 20, 1998

[54] ACTIVATED HUMAN FACTOR VIII AND METHOD OF PREPARATION

[75] Inventors: Joseph Edward Curtis, Glendora; Sam Leland Helgerson, Pasadena, both of Calif.

[73] Assignee: Baxter International Inc., Deerfield, Ill.

[21] Appl. No.: 470,173

[22] Filed: Jun. 6, 1995

Related U.S. Application Data

[63] Continuation of Ser. No. 96,332, Jul. 23, 1993, abandoned.

[51] Int. Cl.$^6$ ................................................ A61K 35/14
[52] U.S. Cl. ......................... 530/383; 530/416; 530/402; 435/68.1
[58] Field of Search ........................ 435/68.1; 530/383, 530/416, 402

[56] References Cited

U.S. PATENT DOCUMENTS

| | | | |
|---|---|---|---|
| 4,386,068 | 5/1983 | Mitra et al. | 530/383 |
| 4,387,092 | 6/1983 | Liautaud et al. | 530/383 |
| 4,404,131 | 9/1983 | Schwarz et al. | 530/383 |
| 4,508,709 | 4/1985 | Amphlett et al. | 530/383 |
| 4,649,132 | 3/1987 | Zimmerman et al. | 514/12 |
| 4,757,006 | 7/1988 | Toole, Jr. et al. | 435/69.6 |
| 4,758,657 | 7/1988 | Farb et al. | 530/383 |
| 4,769,336 | 9/1988 | Zimmerman et al. | 436/518 |
| 4,795,806 | 1/1989 | Brown et al. | 530/383 |
| 4,831,119 | 5/1989 | Nordfang et al. | 530/383 |
| 4,857,635 | 8/1989 | Zimmerman et al. | 530/383 |
| 4,868,112 | 9/1989 | Toole, Jr. | 435/69.6 |
| 4,980,456 | 12/1990 | Scandella et al. | 530/383 |
| 4,981,951 | 1/1991 | Tsay | 530/383 |
| 5,101,016 | 3/1992 | Zimmerman et al. | 530/383 |
| 5,149,687 | 9/1992 | Scandella et al. | 435/69.6 |
| 5,278,289 | 1/1994 | Johnson et al. | 530/383 |
| 5,484,890 | 1/1996 | Johnson et al. | 530/383 |
| 5,576,291 | 11/1996 | Curtis et al. | 514/12 |

FOREIGN PATENT DOCUMENTS

| | | |
|---|---|---|
| 0123945 A1 | 7/1984 | European Pat. Off. . |
| WO88/08035 | 10/1988 | WIPO . |
| WO 93/10143 | 5/1993 | WIPO . |

OTHER PUBLICATIONS

Journal of Biological Chemistry—vol. 269, No. 8, 25 Feb. 1994, pp. 6246–6251 "Isolation and Characterization of Thrombin–activated Human Factor VIII".

Curtis et al. Structural Studies of Human Factor VIII Activation etc. Protein Society, Jul. 1992.

Wang, Y–C.J. et al. *J. of Parenteral Science & Technology*, vol. 42, No. 25, pp. 52–526 (1988).

Pittman et al. A2 Domain of Human Recombinant–Derived Factor VIII etc. Blood, vol. 79, No. 2, pp. 389–397, Jan. 15, 1992.

Scandella et al. Human Factor VIII Inhibitors: Further Epitope etc., Thrombosis Haemostasis, vol. 58, Issue 1, p. 520, 1987.

Curtis et al. Characterization of a Stable Preparation of Thrombin– etc., American Society of Hematology Meeting, Anaheim, California, Dec. 8, 1992.

Tuddenham et al. The Properties of Factor VIII Coagulant Activity etc., The C.V. Mosby Company, J. Lab. Clin. Med. vol. 93, No. 1, pp. 40–43, Jan. 1979.

Weinstein et al. Analysis of Factor VIII Coagulant Antigen etc., Proc. Natl. Acad. Sci. USA, vol. 78, No. 8, pp. 5137–5141, Aug. 1981.

Vehar et al. Structure of Human Factor VIII Nature vol. 312, pp. 337–342, Nov. 22, 1984.

Fulcher et al. Localization of Human Factor VIII Inhibitor etc. Proc. Natl. Acad. Sci. USA, vol. 82, pp. 7728–7732, Nov. 1985.

Brinkhous et al. Purified Human Factor VIII Procoagulant Protein etc. Proc. Natl. Acad. Sci. USA, vol. 82, pp. 8752–8756, Dec. 1985.

Eaton et al. Construction and Characterization of an Active Factor etc. Biochemistry, vol. 25, No. 26, pp. 8343–8346, Dec. 30, 1986.

Eaton et al. Characterization of Recombinant Human Factor VIII The J. of Biological Chemistry, vol. 262, No. 7, pp. 2385–3290, Mar. 5, 1987.

Nordfang et al. FVIII Subunits: Purification and Antigenic Properties Thrombosis and Haemostasis 58 (4) 1043–1048, 1987.

Scandella et al. Epitope Mapping of Human Factor VIII Inhibitor etc. Proc. Natl. Acad. Sci. USA, vol. 85, pp. 6152–6156, Aug. 1988.

Lollar et al. Subunit Structure of Thrombin–Activated Porcine etc. Biochemistry 1989, 28, 666–674.

White et al. Factor VIII Gene and Hemophillia a Blood Reviews (1989) 3, 180–191; Blood vol. 73, No. 1, pp. 1–12, Jan. 1989.

Bihoreau et al. Isolation and Characterization of Differenct etc. Eur. J. Biochem. 185, 111–118 (1989) Feb.

Scandella et al. Localization of Epitopes for Human Factor VIII etc. Blood, vol. 74, No. 5, Oct. 1989, pp. 1618–1626.

Tuddenham, Factor VIII and Haemophilia A Bailliere's Clinical Haematology, vol. 2, No. 4, Oct. 1989, pp. 849–877.

Kaufman, Genetic Engineering of Factor VIII Nature vol. 342, 9 Nov. 1989, pp. 207–208.

Nordfang, Coagulation Factor VIII European J. of Heamatology, Supplementum No. 49, vol. 43, 1989.

Lollar et al. PH–Dependent Denaturation of Thrombin–Activated etc. The J. of Biological Chemistry, vol. 265, No. 3, pp. 1688–1692, Jan. 25, 1990.

(List continued on next page.)

*Primary Examiner*—Robert A. Wax
*Assistant Examiner*—Enrique D. Longton
*Attorney, Agent, or Firm*—Janice Guthrie

[57] ABSTRACT

A method for preparing a purified and stable activated human Factor VIII composition is disclosed. A purified and stable activated human Factor VIII composition having a specific activity of at least 100,000 units per mg protein, or a potency of at least 15,000 units per ml is also disclosed.

6 Claims, 3 Drawing Sheets

OTHER PUBLICATIONS

Foster et al. Synthetic Factor VIII Peptides with Amino Acid etc. Blood, vol. 75, No. 10, pp. 1999–2004, May 15, 1990.

Kemball–Cook et al. Factor VIII Heavy Chain Polypeptides in Plasma etc. British Journal of Haematology, 1990, 76, 80–87.

Foster et al. A Synthetic Factor VIII Peptide of Eight Amino Acid etc. Thrombosis and Haemostasis, 63 (3) 403–406 (1990).

Krishnan et al. Thrombin Cleavage Analysis of a Novel etc. Eur. J. Biochem. 195, pp. 637–644 (Received 1990) Feb. 1991.

Ingerslev et al. Clinical Experience with Hemofil M in a Hemophillia etc. Ann. Hematol (1991) 63: 52–154.

Fay et al. Human Factor VIIIA Subunit Structure Reconstitution etc. The J. of Biological Chemistry vol. 266, No. 14, pp. 8957–8962, May 15, 1991.

Lollar et al. Structural Basis for the Decreased Procoagulant etc. The J. of Biological Chemistry vol. 266, No. 19, pp. 12481–12486, Jul. 5, 1991.

Fay et al. Characterization of the Interaction Between the A2 Subunit etc. The J. of Biological Chemistry vol. 267, No. 19, pp. 13246–13250, Jul. 5, 1992.

Foster et al. Factor VIII Structure and Function Blood Reviews (1989) 3, 180–191; 1989 Longman Group UK Ltd.

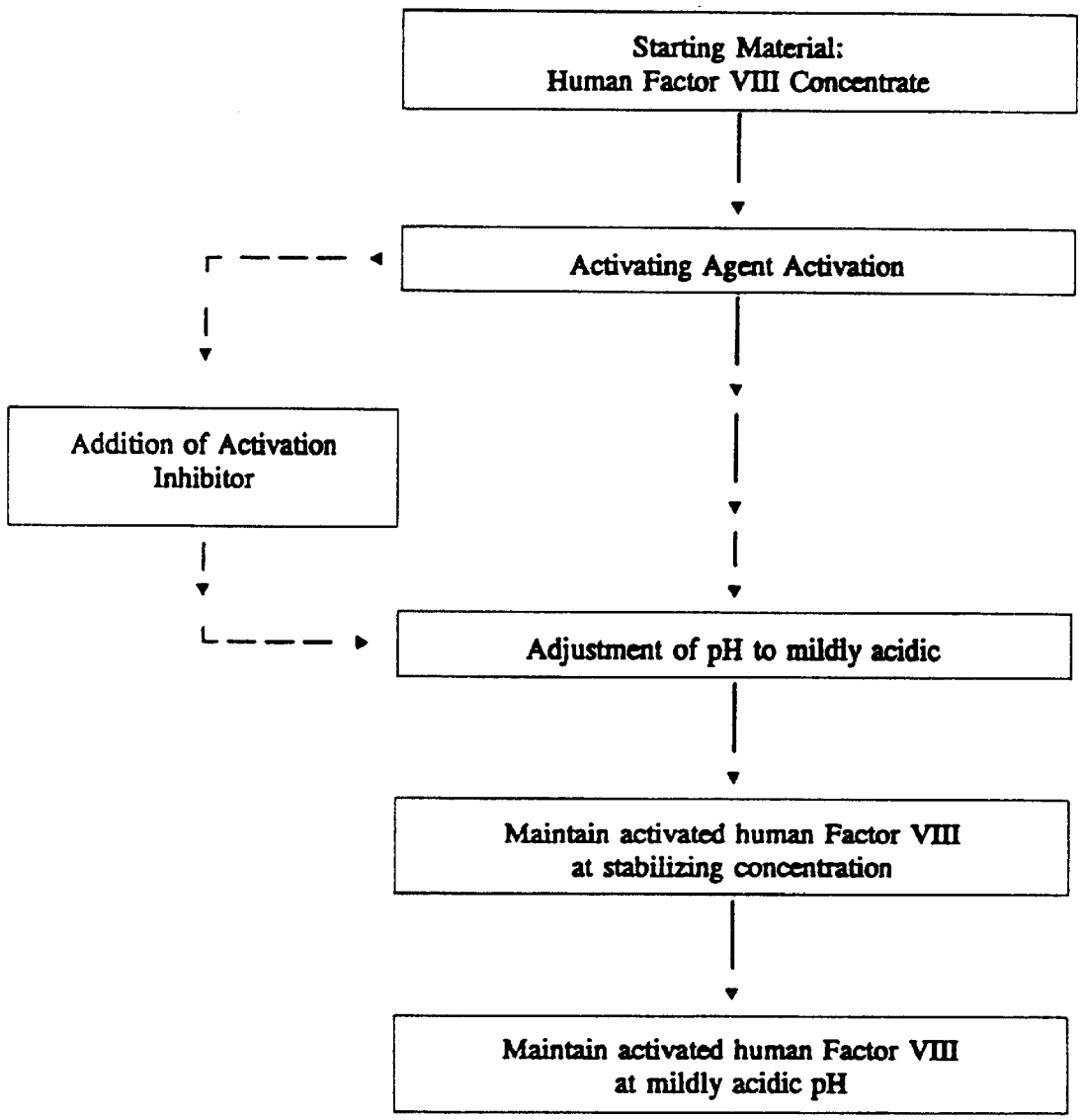
F I G. 1

ACTIVATED HUMAN FACTOR VIII AND METHOD OF PREPARATION

This application is a continuation of U.S. Ser. No. 08/096,332, filed Jul. 23, 1993, now abandoned

TECHNICAL FIELD OF THE INVENTION

This invention relates to a method for preparing the human protein, activated Factor VIII, from Factor VIII derived from blood plasma or from cells modified to express Factor VIII.

BACKGROUND

Hemophilia A is an X chromosome-linked congenital disorder caused by the lack of the biologically active coagulation protein Factor VIII. This factor can be isolated and purified from human blood plasma obtained from donors having normal levels of human Factor VIII or from cell cultures which are genetically engineered to express the Factor VIII protein.

Recent advances in the isolation of Factor VIII and the molecular cloning of the Factor VIII gene have revealed that the primary structure of Factor VIII contains several distinct types of structural domains. There are three A domains, A1, A2, and A3 each of approximately 350 amino acids, a unique region of about 980 amino acids called the B domain, and a carboxyl-terminal region of about 300 amino acids called the C1-C2 domain. These domains are arranged in human Factor VIII in the order of A1- A2-B-A3C1-C2 (Vehar et al. Nature 312:327 to 342, 1984).

Treatment of procoagulant protein Factor VIII with thrombin results in an increase in coagulant activity, which is associated with the formation of an activated form of Factor VIII. Previous attempts to isolate and characterize the activated form of human Factor VIII have been unsuccessful because the activity of this form rapidly decays. The activation of Factor VIII by thrombin has been shown to coincide with cleavage of the polypeptide chain at residue position 372 between the A1 and A2 domains, at position 740 between the A2 and B domains, at unidentified positions within the B domain, and at position 1689 between the B and A3-C1-C2 domains. The active Factor VIII complex then forms as a heterotrimer composed of the A1, A2, and A3-C1-C2 subunits. Recently, Lollar et al. (*Biochemistry* 28: 666 to 674, 1989) isolated an activated form of porcine Factor VIII by reacting the protein with thrombin until the peak coagulant activity was obtained, and then isolated the resulting activated porcine Factor VIII using a strong cationic exchange resin with charged sulfonic groups, such as "MONO S".

Attempts to prepare the activated form of human Factor VIII have not been successful following the same procedure used for porcine Factor VIII. Lollar et al. *J. Biol. Chem.*, 266: 12481 to 12486, 1991; Fay et al. *J. Biol. Chem.*, 266: 8957 to 8962, 1991 and *J. Biol. Chem.*, 267: 13246 to 13250, 1992.

SUMMARY OF THE INVENTION

This invention relates to a method for preparing and isolating stable, highly active human Factor VIII. The human Factor VIII suitable for activation is purified human Factor VIII isolated either from human blood plasma or from cell culture material containing expressed, biologically active recombinant human Factor VIII.

According to the present invention, the process involves activating human Factor VIII by reacting it with an activating agent, and inactivating or removing the activating agent from the presence of the activated Factor VIII. The activated human Factor VIII is then maintained at a mildly acidic pH and at a stabilizing concentration. The preparation can be lyophilized or frozen at −80° C.

The present method yields an activated human Factor VIII with a specific activity greater than 100,000 units/mg which can be formulated at a potency greater than 15,000 units/ml. Use of activated human Factor VIII avoids the necessity of in vivo activation of the Factor VIII procoagulant protein by uncontrolled proteolysis. When infused, the activated Factor VIII can assemble as part of the tenase complex which is an essential step in the formation of a fibrin blood clot. This treatment acts to control bleeding associated with the hemostatic defect caused by a deficiency of the biologically active blood coagulation factor.

BRIEF DESCRIPTION OF FIGURES

FIG. 1 is a schematic diagram of the process for preparing activated human Factor VIII from human Factor VIII.

DETAILED DESCRIPTION OF THE INVENTION

Figure 2:
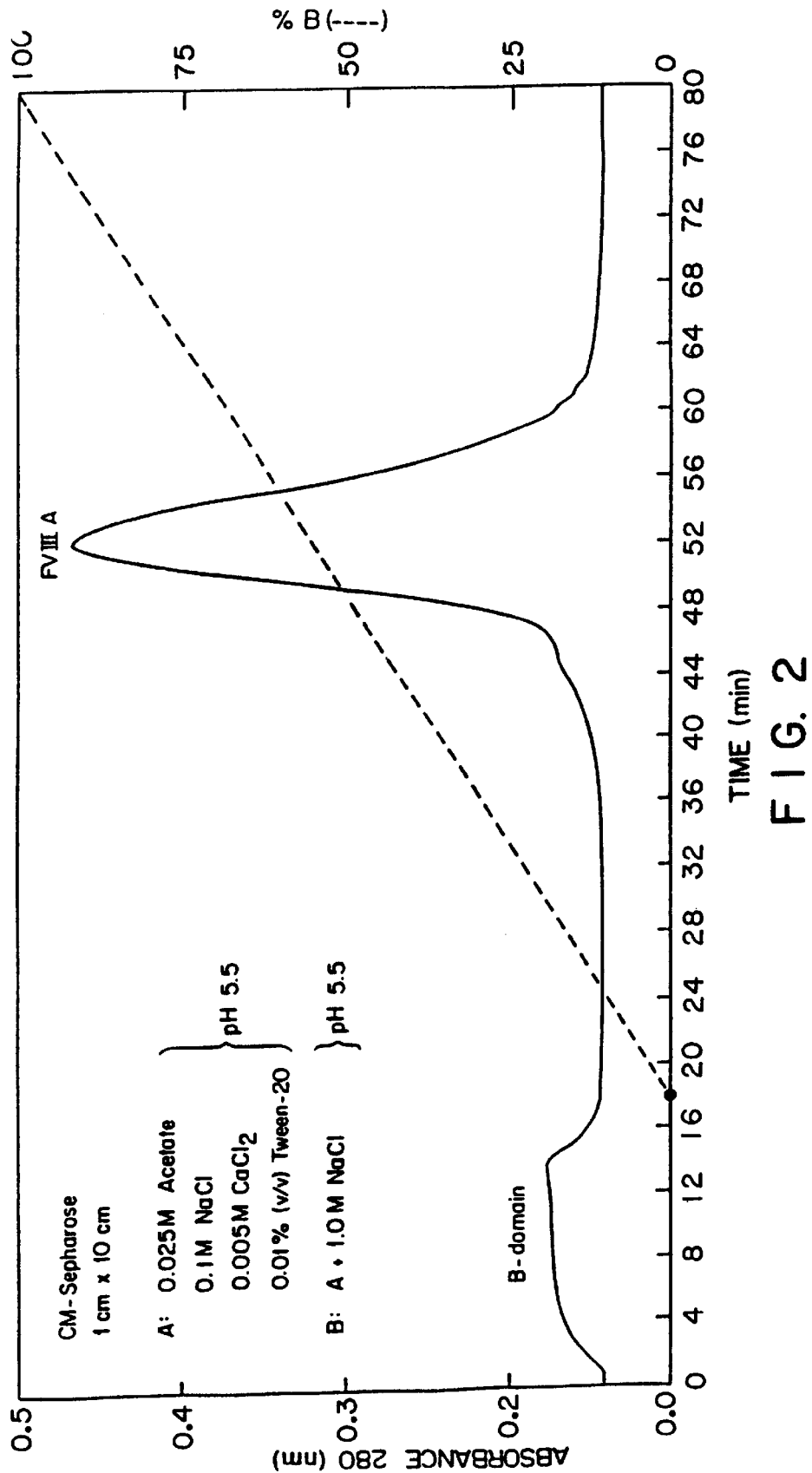
FIG. 2 shows the elution pattern of activated human Factor VIII from a cationic exchange resin.

The invention comprises a method such as shown in FIG. 1 for producing a stabilized activated human Factor VIII. The method comprises activating human Factor VIII with an activating agent, inactivating or removing the active activating agents from the presence of the activated Factor VIII, adjusting the pH of the activated Factor VIII solution to a mildly acidic pH, and maintaining the activated Factor VIII at a stabilizing concentration. The activated Factor VIII obtained by this process has high coagulant Factor VIII specific activities greater than 100,000 units/mg, and can be formulated at potencies greater than 15,000 units/ml, a formulation not previously possible.

Herein, the term human Factor VIII denotes a functional protein capable of in vivo or in vitro correction of human Factor VIII deficiencies characterized, for example, by hemophilia A. Factor VIII includes the Factor VIII sequence shown in "Structure of Human Factor VIII" Nature 312: 339, FIG. 3. Thrombin fragmentation of the Factor VIII molecule is illustrated by a line diagram in "Structure of Human Factor VIII" *Nature* 312: 341, FIG. 6 or by a block diagram in "Genetic Engineering of Factor VIII" Nature 342: 207, FIG. 1.

The starting material for the process of this invention can be any purified human Factor VIII protein which can be converted to an active heterotrimer form containing the A1, A2, and A3-C1-C2 domains of Factor VIII as subunits. The subunits have molecular weights of about 50 kD for the A1, about 43 kD for the A2, and 73 kD for the A3-C1-C2. The starting human Factor VIII protein is typically derived from human plasma or from cell culture material containing functional Factor VIII protein.

One type of Factor VIII useful herein is the recombinant protein generated in cell culture using genetically modified cells. Methods for expressing functional human Factor VIII in cell culture are known and described in U.S. Pat. Nos. 4,868,112; 4,757,006; and 4,965,199; European publication number EP 0150735; PCT publication numbers WO91/09122 and WO91/00347; Eaton et al. "Construction and Characterization of an Active Factor VIII Variant Lacking the Central One-Third of the Molecule" *Biochemistry* 25: 8343 to 8347; and Krishnan et al. "Thrombin Cleavage Analysis of a Novel Antihaemophilic Factor Variant Factor VIIIΔII" *Eur. J. Biochem.* 195: 635 to 644. The foregoing publications show examples of expressed human Factor VIII and variant forms of human Factor VIII which can be used with the invention.

Methods for purifying the native human Factor VIII from plasma or from cell culture-derived human Factor VIII are also described in the prior art. The literature reciting the various methods for expressing functional human Factor VIII in cell culture material also illustrate the methods used for purifying the expressed human Factor VIII molecule. Additionally, a variety of methods are known for isolating and purifying human Factor VIII which may be used as starting material in the practice of this invention (U.S. Pat. Nos. 4,965,199; Re 32,011; 4,495,175; 4,758,657; 4,508,709; and 4,981,951; Bihoreau et al., "Isolation and Characterization of Different Activated Forms of Factor VIII, the Human Antihemophilic A Factor" *Eur. J. Biochem.* 185: 111 to 118; Tuddenham et al., "The Properties of Factor VIII Coagulant Activity Prepared by Immunoadsorbent Chromatography" *J. Lab. Clin. Chem.* 99: 40 to 53).

The purified human Factor VIII used as the starting material in this invention may be suspended in different buffer compositions, depending upon the purification method used. The purified human Factor VIII solution may be dialyzed with a buffer solution such as a solution containing 0.15M sodium chloride, 20 mM Hepes, and 5 mM $CaCl_2$ prior to activation by an activating agent.

The method for producing activated stable Factor VIII starts with the activation of purified human Factor VIII. The term "activation" refers to the reaction of the activating agent with human Factor VIII to produce the activated form. One suitable technique for producing the activation comprises the use of an activating agent which cleaves the Factor VIII protein at the preferred sites between the A1 and A2 subunits, between the A2 and B subunits, and at the amino terminus of the A3 subunit.

The activating agents useful in the practice of this invention are those substances which specifically cleave the Factor VIII molecule at the aforementioned residue position 372 between the A1 and A2 domains, at position 740 between the A2 and B domains, and at position 1689 between the B and A3-C1-C2 domains. Examples of activating agents are particularly serine proteases such as thrombin, trypsin, plasmin, and activated Factor IX, but may include other proteases, catalytic antibodies, or ribozymes.

The activating agent should be used under conditions where it is capable of cleaving the Factor VIII bonds to produce the desired subunits. When thrombin is used as the activating agent, it has been found to be active at a pH between about 5 and 10, preferably slightly above 7, such as 7.2 to 8, and more preferably about 7.4 or 7.5. Other activating agents will have a maximum reactivity with Factor VIII at conditions readily ascertainable in the art.

The activating agents which activate Factor VIII should be removed from the presence of the activated protein to reduce and preferably eliminate further protein degradation to inactive forms. Techniques for removing activating agents are discussed herein, but generally the activating agents should be removed or otherwise inactivated to such an extent that activated Factor VIII is not further reactive with the activating agent. In addition to removing the activating agents, they can also be inactivated or inhibited to such an extent that they are no longer reactive with the Factor VIII molecule or its activated form.

The extent of quantitative removal or inactivation of the activating agent will depend upon the agent selected and the characteristics of the activated Factor VIII composition. As shown in Example 1, using thrombin as the activating agent, it has been found acceptable to remove 90% of the thrombin activity. A preferred embodiment of the process of this invention comprises isolating the activated Factor VIII, after its formation, from the other proteins and proteolytic fragments present in the mixture, as well as from the activating agent. Isolation techniques are well known, and one preferred isolation technique used herein is binding the activated Factor VIII to a cationic exchange column, removing all of the other components of the activated Factor VIII medium, and eluting the activated Factor VIII in a purified form.

In a preferred embodiment, a 30 to 1 molar ratio of human Factor VIII to thrombin can be reacted at a pH slightly above 7. Human Factor VIII starting material is present, preferably in a concentration of about 25 to 1000 IU/ml, more preferably from about 100 to 1000 IU/ml, and/or a specific activity from about 2 to the estimated specific activity for completely pure Factor VIII, which is about 8000 IU per mg protein, preferably about 1000 to 8000 IU/mg protein. At these concentrations and activities, temperatures from about 0° C. to about 45° C., preferably about 37° C., for at least 30 seconds is sufficient to activate human Factor VIII. The time required for activation varies, depending upon the temperature of the reaction and the molar ratio of Factor VIII to thrombin. Switzer et al., "Effects of Thrombin on Factor V and Factor VIII, Chemistry and Biology of Thrombin" in *Chemistry and Biology of Thrombin* ed. by R. L. Lundblad, J. W. Fenton, II and K. G. Mann, *Ann Arbor Science*, Michigan, pp. 331 to 333, 1977). To achieve maximum activation and recovery, the optimum reaction time can be determined by monitoring the increase of Factor VIII activity during the activation step. Once peak Factor VIII activity is achieved, the pH of the solution is promptly adjusted to a mildly acidic pH, preferably between 4.0 and 6.5, and more preferably from about 5.5 to 6. The activation reaction may be terminated by adding an activating agent inhibitor. Examples of suitable inhibitors for thrombin are PPACK, heparin cofactor II, hirudin, antithrombin III, and derivatives of sulfonylfluoride. Inhibitors are added at a molar concentration in excess of the moles of activating agent added for the activation, preferably at a concentration of about three moles of inhibitor per one mole of activating agent.

Alternatively or in addition to inhibition of the activating agent activity, the activated Factor VIII may be directly contacted with a cationic exchange resin containing carboxymethyl or sulfonic groups to adsorb the activated Factor VIII. The activated human Factor VIII is adsorbed on the surface of the cationic exchange resin pre-equilibrated at the same pH as the activated Factor VIII solution. Herein, equilibration of the cationic exchange resin means extensive washing of the cationic resin with buffer such that the wash buffer after contact with the cationic exchange resin has substantially the same pH and ionic strength as the source buffer solution. Suitable buffers for resin equilibration are those with a pKa below 6 but above 3. Examples of buffers are succinic acid, sodium acetate, and cacodylic acid. A preferred equilibration buffer is sodium acetate at pH 5.5 containing 5 millimolar calcium chloride.

The adsorbed activated human Factor VIII is eluted from the cationic exchange resin with the equilibration buffer to which is added a salt at a concentration sufficient to release activated Factor VIII from the resin. Concentrations of at least 0.5 molar NaCl have been found satisfactory for this purpose. Suitable salt equilibration buffers are the alkali metal salts, such as the salts of lithium, sodium, and potassium. The elution may be conducted with a salt gradient elution using the equilibration buffer with increasing salt concentrations from 0.1 molar to 1.0 molar.

The activated Factor VIII eluted from the cationic exchange resin is adjusted, if necessary, to a pH preferably between 4 and 6.5, and more preferably between about 4.5 and 6. A typical salt elution pattern is shown in FIG. 2.

Use of acetate metal salts, such as sodium or potassium acetate, as the equilibration buffer instead of histidine HCl used by prior art workers, has produced an elution of activated human Factor VIII in a heterotrimeric structure undepeleted of the A2 fragment, thereby making unnecessary the addition of A2 to a predominantly A1/A3-C1-C2 dimer mixture to restore maximum coagulant activity. This heterotrimer can exist in equilibrium with disassociated subunits in such a manner that the preparation containing activated Factor VIII will usually contain both the A1/A2/A3-C1-C2 trimer and the individual subunits and dimeric forms thereof. The weight ratios of the heterotrimer to smaller units of dimer and monomer at equilibrium vary depending upon physical and chemical conditions, but are typically from about 100% heterotrimer to 0% smaller units, to a ratio of about 50% heterotrimer to 50% smaller subunits.

At a number of points in the process, protein stabilizers can be added to the Factor VIII and its activated form to further reduce or eliminate the formation of degradation products from the desired activated Factor VIII product. Examples of stabilizers include albumin, sucrose, maltose, glycine, and trehalose. If protein stabilizers are used in the compositions, the specific activity of the compositions is calculated by determining the total protein content less the amount of added protein stabilizer if any remains in the composition. Following the preparation and stabilization of the activated Factor VIII, the protein can be lyophilized and stored at reduced temperatures until the protein is to be administered, at which time it can be redissolved in sterile solution for administration.

Also important is the degree of activity and stability of the activated Factor VIII once it is isolated. Activated Factor VIII having a specific activity greater than 100,000 and even greater than 200,000 units/mg protein have been prepared. The activated Factor VIII preparations can be formulated to have potencies greater than 15,000 and also greater than 30,000 units/ml and even greater than 200,000 units/ml of solution.

One of the principal features of this invention resides in the preparation of the highly active Factor VIII in a concentrated and stabilized form. Stability for purposes of this invention means an activated Factor VIII which retains a level of its activity long enough to be administered to patients and produce a hemostatic effect. Depending upon the means of Factor VIII activation, stability of activated Factor VIII capable of producing a hemostatic effect can be as short as several seconds if the activated Factor VIII is formed in a receptacle such as a hypodermic syringe, or even immediately upon ejection from such a receptacle prior to or during injection into a patient. Also included within the scope of this invention are stabilized activated Factor VIII preparations which are stable for several weeks, thereby permitting the packaging of the activated Factor VIII for administration at a later date.

Stability is also measured in terms of the percentage of specific activity retained over a period of time. Preferred compositions retain at least 50%, and preferably at least 80%, of their specific activity for at least one month, preferably at least one year, following their activation.

The stability of activated Factor VIII is influenced by a number of conditions. The stability of the purified activated Factor VIII can be enhanced by achieving a certain minimum concentration of the activated Factor VIII in solution. To achieve the additional stability of the protein through concentration in solution, the activated Factor VIII should be at least 0.1 micromolar, preferably at least 0.2, and even more preferably at least 1.0 micromolar. Under other processing conditions, the concentration of the activated Factor VIII can vary from the above guidelines.

Other conditions affecting stability are the pH of the final activated solution, the absence of an active activating agent, a low concentration of multivalent cations and the conditions of storage. The pH of the solution should be adjusted and kept at a mildly acidic condition, preferably at a pH between about 4 and 6.5, and more preferably between about 4.5 and 6.0. The multivalent cations should preferably be present at a maximum concentration of about 20 millimolar and more preferably at least 5 millimolar. Representative cations are calcium, other alkali earth metals, and transition metals such as iron, chromium, copper, zinc, manganese and the like.

Temperature of storage and exposure to UV radiation are two external conditions which can be controlled to maintain activity of the activated Factor VIII preparations. Generally, temperatures of 25° C. or less and UV exposure minimized by enclosure in an opaque container such as a box are preferred. Lyophilization following activation, optionally followed by storage at a reduced temperature, such as −80° C., is also effective in producing a stable activated Factor VIII preparation.

If the activated Factor VIII solution is to be used for human or animal administration, the solution can be filtered through a sterilizing filter to remove microorganisms. The term "sterilizing filter" refers to a membrane device with pore sizes averaging 0.2 micron in diameter which will retain bacteria and larger microorganisms while allowing the activated human Factor VIII solution to pass through. A more porous filter may be used if the activated solution is intended as a laboratory reagent for diagnostic or research use. The more porous filters are filter membrane devices with pore sizes typically of 0.45 or 0.5 micron diameter or larger.

The activated and stabilized human Factor VIII preparations of this invention are useful as hemostatic agents. All of the many uses and benefits of Factor VIII can also be attained with activated and stabilized Factor VIII, with occasional modification of storage and administration conditions, which may be advised in view of the differences in concentration and specific activity of the two substances.

EXAMPLE 1

Bulk human recombinant Factor VIII obtained from Baxter Healthcare Corporation, Hyland Division, was used as the starting Factor VIII material. The same material formulated in therapeutic dosage form is available under the trademark Recombinate™. The Factor VIII at a concentration of 0.4 mg/ml in 0.4M NaCl, 20 mM Tris-HCl 5 mM $CaCl_2$ and 0.01% v/v Tween-20 at pH 7.4 was first dialyzed overnight at 4° C. into 0.15M NaCl, 20 mM Hepes buffer and 5 mM $CaCl_2$ at pH 7.4. The dialyzed Factor VIII was stored at −20° C. until use. Factor VIII (31 nmole) was activated by digestion with human thrombin (1. nmole) for 10 minutes at 37° C. Activation was stopped by addition of 10 ml of 100 mM Na acetate buffer adjusted to pH 5.5. The sample was then loaded onto a CM-Sepharose column at 2 ml/min using a 50 ml Superloop column (FPLC Chromatography System, Pharmacia, Piscataway, N.J.). The column was pre-equilibrated with Buffer A (25 mM Na acetate, 100 mM NaCl, 5 mM $CaCl_2$, 0.01 % v/v Tween-20, pH 5.5). The sample was eluted from the column using a linear salt gradient from 0.1M NaCl in Buffer A to 1.0M NaCl in Buffer B (25 mM Na acetate, 1.0M NaCl, 5 mM $CaCl_2$, 0.01% v/v Tween-20, pH 5.5). The gradient was run from 0 to 100% Buffer B in 60 minutes at a flow rate of 0.5 ml/min and the eluted peaks were detected by absorbance at 280 nm. The fraction containing the activated Factor VIII eluted between 40 and 60% Buffer B. The activated Factor VIII fraction was collected and stored at −80° C. The activated human Factor VIII had a potency of 30,000 units/ml.

EXAMPLE 2

The starting material for the purification of human activated Factor VIII was bulk human recombinant Factor VIII obtained from Baxter Healthcare Corporation, Hyland Division (Glendale, Calif.). Factor VIII (0.4 mg/ml) in 0.4M NaCl, 20 mM Tris-Cl, 5 mM $CaCl_2$, 0.01% v/v Tween-20 pH 7.4 was first dialyzed into 0.15M NaCl, 20 mM Hepes, 5 mM $CaCl_2$, pH 7.4 overnight at 4° C. The dialyzed Factor VIII was stored at −20° C. until use. Factor VIII (6.2 nmole) was activated by digestion with human thrombin which was previously coupled to agarose beads (using CNBr activated agarose, 1.32 mg/ml resin, Biorad, Richmond, Calif.) for 60 minutes at 37° C. Following activation, the mixture was filtered through MillexGV4 0.22 micron filter unit (Millipore, Bedford, Mass.) to remove the thrombin-agarose suspension. The filtered flow-through solution contained the activated Factor VIII protein. A 2 niL aliquot of 100 mM Na acetate buffer was added to adjust this solution to pH 5.5. The sample was then loaded onto a CM-Sepharose column at 2 ml/min using a 50 ml superloop (FPLC Chromatography System, Pharmacia, Piscataway, N.J.). The column was pre-equilibrated with Buffer A (25 mM Na acetate, 100 mM NaCl, 5 mM $CaCl_2$, 0.01% v/v Tween-20, pH 5.5). The step gradient was run from 0 to 75% Buffer B in 1 minute at a flow rate of 0.5 ml/min and the eluted peaks were detected by absorbance at 280 nm. The fraction containing activated Factor VIII eluted promptly following the application of the step gradient. The activated Factor VIII fraction was collected and stored at −80° C. The activated human Factor VIII had a potency of 30,000 units/ml.

EXAMPLE 3

Activated Factor VIII was subjected to reverse phase chromatography to determine the physical composition of the protein isolated according to the method described in Example 1. A reverse phase high pressure chromatography system (rpHPLC: Waters 484 Tunable Absorbance Detector, Waters 590 Pumps, Waters System Interface Module, and Maxima 820 Chromatography Software) was used to equilibrate a VyDac 0.4 cm X 15 cm C4 column in 75% Buffer A (0.15% trifluoroacetic acid [TFA] in HPLC grade $H_2O$) and 25% Buffer B (0.15% TFA+90% acetonitrile in HPLC grade $H_2O$) at a flow rate of 1.5 ml/min. Following the injection of 0.5 ml activated Factor VIII solution, a linear gradient from 25% to 75% Buffer B over a 25 minute period was used to elute and separate the A1, A2, and A3-C1-C2 subunits of activated Factor VIII. The three subunits eluted at about 16, 17, and 19 minutes, respectively.

The individual subunits were collected and the N-terminal amino acid residues were sequenced using an automated protein microsequencer (Model ABI 477A) and derivatized-amino acid analyzer (Model ABI 120A, Applied Biosystems, Foster City, Calif.). The N-terminal amino acid residues obtained were in agreement with those predicted from the Factor VIII cDNA sequence shown in Vehar et al., Nature 312:327 to 342, 1984.

EXAMPLE 4

Figure 3:
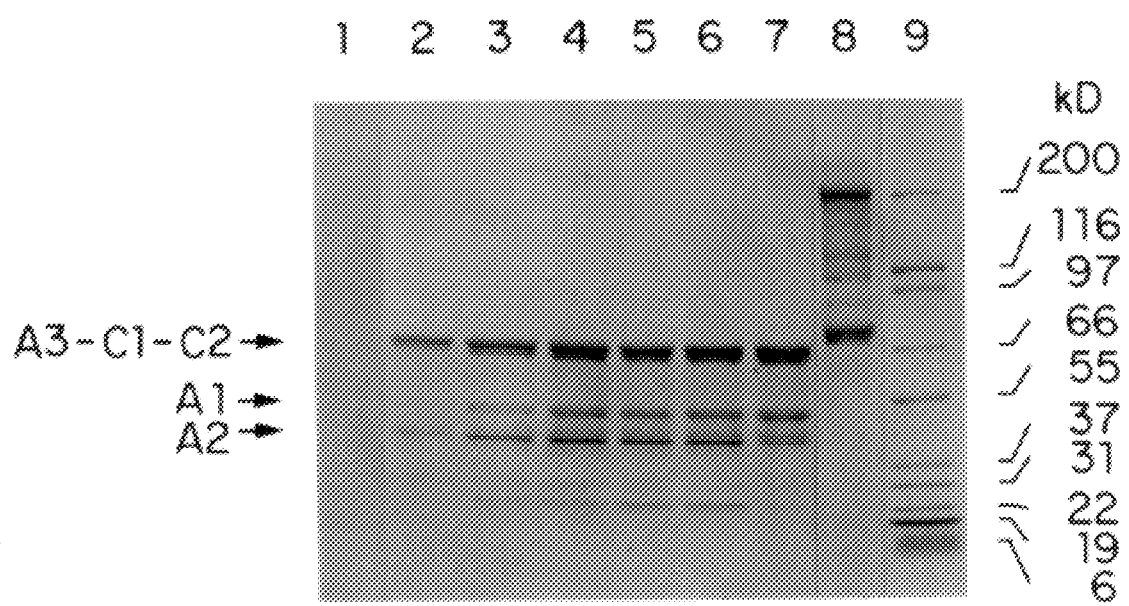
FIG. 3 shows the separation of activated human Factor VIII subunits by SDS polyacrylamide gel electrophoresis.

To determine the subunit composition of activated Factor VIII after isolation by CM-Sepharose chromatography at several different pH values, including pH 5.5, aliquots of activated Factor VIII were subjected to SDS-polyacrylamide gel electrophoresis (SDS-PAGE). Factor VIII was reacted with thrombin, according to the method described in Example 1, at pH 7.4. In this experiment, PPACK inhibitor (Cal Biochem, San Diego) was added, and the pH was changed by the addition of equal volume of 0.1M acetate buffer having the desired pH as listed in FIG. 3. Approximately 20 microliters of sample containing Factor VIII and activated Factor VIII, isolated at different pH values, and molecular weights standards were added to 20 microliters of 2X loading buffer (Novex, San Diego, Calif.) which included 0.3M β-mercaptoethanol. Samples were then denatured by boiling for 5 minutes at 100° C. After cooling, 20 microliters of each sample was loaded into a separate well on a 4 to 12% gradient SDS-PAGE gel (Novex, San Diego, Calif.). The gel was run at 125 volts for 1.5 hours. The gel was stained with Coomassie Brilliant Blue (40% methanol, 10% acetic acid, 0.05% (w/v) Coomassie Brilliant Blue) for one hour. The gel was then destained by washing in 40% methanol, 10% acetic acid overnight. Lanes 1 through 7 of FIG. 3 are activated Factor VIII samples isolated at different pH values. Lane 1, pH 3.5; Lane 2, pH 4.5; Lane 3, pH 4.7; Lane 4, pH 5.0; Lane 5, pH 5.5; Lane 6, pH 6.0; Lane 7, pH 7.4. Lane 8 is Factor VIII pH 7.4, and Lane 9 has molecular weight standards. The results shown in FIG. 3 indicate that activated human Factor VIII when prepared according to the method described in Example 1 has equal amounts of each of the subunits which are required for full functional activity.

EXAMPLE 5

The coagulant activity of activated human Factor VIII was measured in an in vitro modified one stage coagulation assay using activated partial thromboplastin (APTT, Organon Teknika, Durham, N.C.) and commercially available Factor VIII deficient plasma (F8DP, George King Biomedical, Overland Park, Kans.). Standard curves were generated using normal pooled plasma control (FACT, George King Biomedical, Overland Park, Kans.). A quantity of 100 microliters of APTT was added to 100 microliters of F8DP and the mixture was incubated for five minutes at 37° C. Immediately prior to calcium addition, unknown samples were diluted to aliquots containing an estimated 1 unit/ml, and a 10 microliter aliquot of the diluted unknown was added to the APTT/F8DP mixture, followed by 100 microliters of 0.020M $CaCl_2$ pre-warmed to 37° C. The clot time was measured from the addition of calcium to the formation of the first visible fibrin polymers. Standard curves were constructed using several dilutions of FACT (1, ⅓, ⅙, 1/21 units/ml) and plotting the observed clot times versus dilution on a log—log scale. One unit of activated Factor VIII was defined as the amount of material which gives a clot time of 55 to 60 seconds.

EXAMPLE 6

To determine the specific activity, reported as units per milligram of protein, of activated human Factor VIII, the potency in units/ml obtained in Example 5 is divided by the amount of activated Factor VIII protein. The amount of activated Factor VIII protein is determined from the absorbance at 280 nanometers using the extinction coefficient at 280 nanometers of activated Factor VIII which was been determined to be 1.60 ml×mg$^{-1}$×cm$^{-1}$. The concentration is determined using Beer's Law: C=A/eL (C, concentration in mg/ml; A, absorbance at 280 nanometers; e, extinction coefficient at 280 nanometers; and L, path length in centimeters).

EXAMPLE 7

Activated Factor VIII prepared according to the method described in Example 1 was analyzed by size exclusion chromatography to determine the approximate molecular weight of activated human Factor VIII. A size exclusion high pressure liquid chromatography system (SE-HPLC: Waters 991 Photodiode Array Detector, Waters 600E System Controller, and Waters Chromatography Software) was used to equilibrate a Toso Haas size exclusion column (G3000SW$_{XL}$ 7.8 mm$_{ID}$×30 cm) in running buffer (0.7M NaCl, 0.025M acetate, 0.005M CaCl$_2$, 0.01% (v/v) Tween-20, pH 5.5) at a flow rate of 1.0 ml/min. A standard curve was generated using a marker protein kit from United States Biochemical (Cleveland, Ohio). The least squares best fit line to the standard curve was determined to be MW in kiD=740–60 (retention time in minutes). The retention time was found to be 9.8 minutes. Therefore the approximate molecular weight of activated human Factor VIII in this Example was 150 kD.

We claim:

1. A method of producing an activated and stabilized human Factor VIII protein having a specific activity of at least 100,000 units per mg comprising:
   (a) activating human Factor VIII in a solution containing other proteins by contacting said Factor VIII with an activating agent which specifically cleaves the human Factor VIII molecule at amino acid residue position 372 between the A1 and A2 domains, at position 740 between the A2 and B domains, and at position 1689 between the B and A3-C1-C2 domains;
   (b) removing said agent, other proteins, and proteolytic fragments from the presence of the activated Factor VIII by adsorbing the activated Factor VIII on a carboxymethyl cationic exchange resin while removing said agent, other proteins, and proteolytic fragments;
   (c) maintaining the concentration of the activated Factor VIII at a level of at least 1.0 μM:
   (d) eluting the activated Factor VIII from the cation exchange resin using a buffer selected from the group consisting of succinic acid, sodium acetate, potassium acetate, and cacodylic acid; and
   (e) adjusting the pH of the activated human Factor VIII to pH 4–6.5.

2. The method of claim 1 wherein said activated and stabilized human Factor VIII protein has a potency of at least 15,000 units per ml.

3. The method of claim 1 wherein the activating agent is inactivated with an inhibitor after activation of the human Factor VIII has occurred.

4. The method of claim 1 wherein the activated Factor VIII is additionally stabilized with a stabilizing additive selected from the group consisting of human serum albumin, sucrose, and trehalose during the conduct of the method.

5. The method of claim 1 wherein the activated Factor VIII is lyophilized after the pH of said Factor VIII is adjusted in Step (e).

6. A method of producing an activated and stabilized human Factor VIII protein having a specific activitv of at least 100,000 units per mg comprising:
   (a) providing a solution containing other proteins and subunits of Factor VIII, said subunits comprising A1, A2, and A3-C1-C2;
   (b) removing said other proteins and proteolytic fragments from the presence of the activated Factor VIII by adsorbing the activated Factor VIII on a carboxymethyl cationic exchange resin while removing the other proteins and proteolytic fragments;
   (c) maintaining the concentration of the activated Factor VIII at a level of at least 1.0 μM;
   (d) eluting the activated Factor VIII from the cation exchange resin using a buffer selected from the group consisting of succinic acid, sodium acetate, potassium acetate, and cacodylic acid, and
   (e) adjusting the pH of the activated human Factor VIII to pH 4–6.5.

* * * * *